United States Patent [19]

Machacek

[11] Patent Number: 5,445,163

[45] Date of Patent: Aug. 29, 1995

[54] NEURO-AIDS PINWHEEL

[76] Inventor: Gilbert A. Machacek, 6497 Debbie La., St. Petersburg, Fla. 33707

[21] Appl. No.: 271,074

[22] Filed: Jul. 5, 1994

Related U.S. Application Data

[63] Continuation-in-part of Ser. No. 199,599, Feb. 22, 1994, abandoned.

[51] Int. Cl.⁶ ............................................. A61H 15/00
[52] U.S. Cl. ..................................... 123/744; 601/112; 601/127
[58] Field of Search ............... 128/744; 601/112, 114, 601/118, 119, 120, 127

[56] References Cited

U.S. PATENT DOCUMENTS

| | | | |
|---|---|---|---|
| 1,103,669 | 7/1914 | Gibbs | 601/119 X |
| 1,519,631 | 12/1924 | Sawtelle | 601/119 |
| 1,630,149 | 5/1927 | Wahrt | 601/119 |
| 3,850,163 | 11/1974 | Andis, Sr. | 601/119 |
| 4,744,350 | 5/1988 | Sato | 601/119 |
| 5,316,012 | 5/1994 | Siegal | 128/744 |

FOREIGN PATENT DOCUMENTS

| | | | |
|---|---|---|---|
| 2480118 | 10/1981 | France | 601/119 |
| 664486 | 3/1988 | Switzerland | 601/119 |

*Primary Examiner*—Sam Rimell
*Attorney, Agent, or Firm*—Walter J. Monacelli

[57] ABSTRACT

The pinwheel testing device described herein comprises a disk with sharp points or pins projecting outwardly from the circumference of the disk. This disk is rotatably mounted on a handle so that the sharp points of the disk device can be rolled on a patient's body part to test reaction to pain and sensitivity. Since there sometimes is a puncturing of the skin in the test area, there is great concern about the spread of HIV virus and other blood borne diseases, such as hepatitis, slow-virus, etc. Present instruments used for this purpose are made of stainless steel and, since they cannot be discarded, present a problem to keep them sterile. The design of the pinwheel device described herein makes it possible to make this unit out of plastic and therefore disposable. The manufacture of this device also permits structural advantages not available when such a device is made of metal.

13 Claims, 2 Drawing Sheets

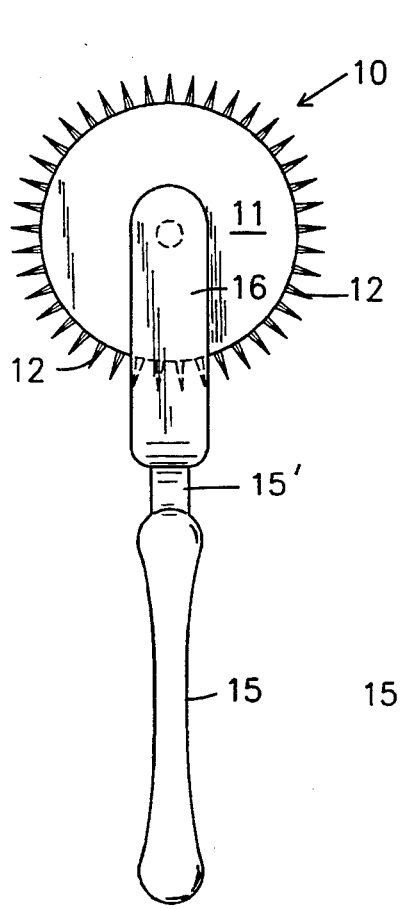
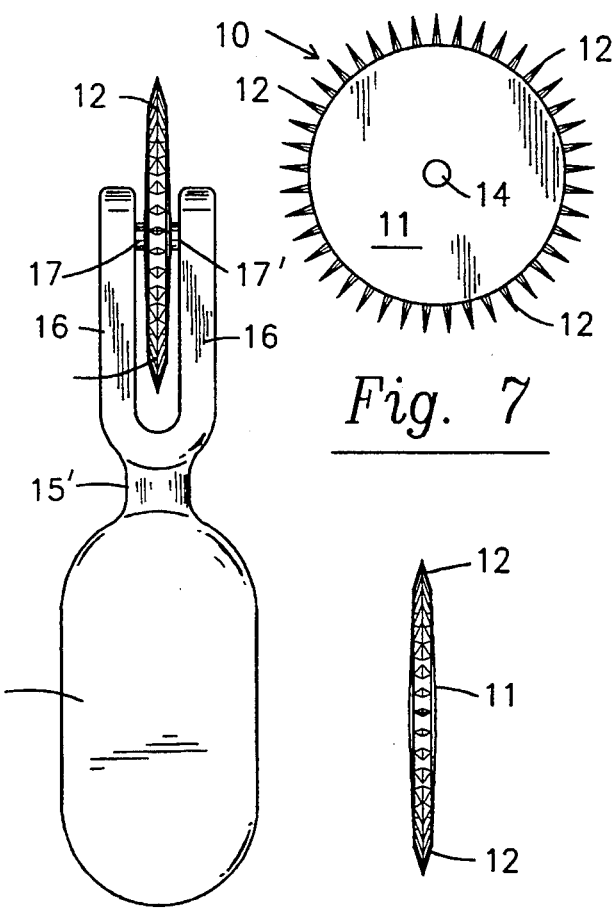
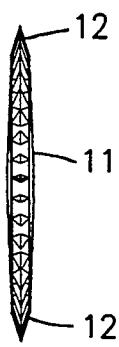
Fig. 5  Fig. 6  Fig. 8
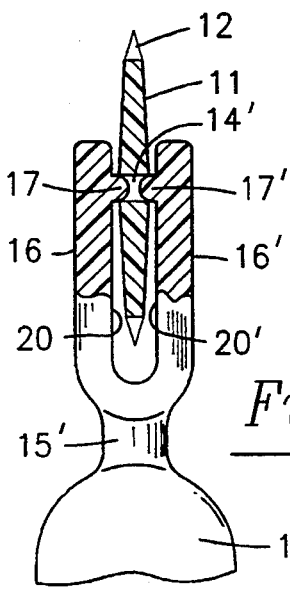
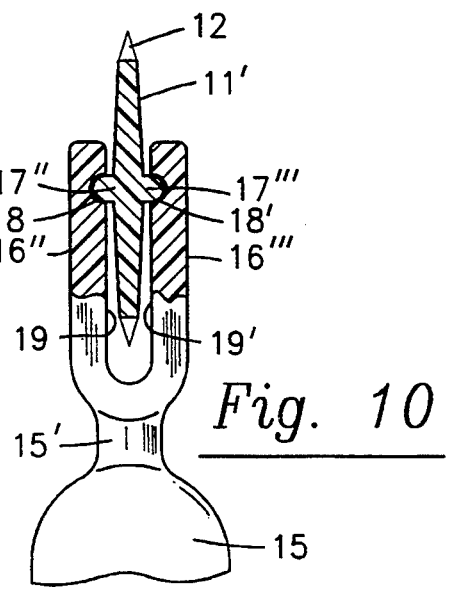
Fig. 9  Fig. 10

NEURO-AIDS PINWHEEL

This application is a continuation-in-part of pending application Ser. No. 08/199,599, filed Feb. 22, 1994.

BACKGROUND

1. Field of the Invention

This invention relates to devices for testing a patient's body for sensitivity and pain. More specifically it relates to a pinwheel type device used for this purpose. Still more specifically it relates to the rolling of such a device having a rotatable pinwheel on an area of a patient's body to test it for pain and sensitivity.

2. Background of the Invention

It is routine within chiropractice to test patients with neuromusculosketal disorders to use a pinwheel apparatus to determine the patient's sensitiveness to pain and touch by running a pinwheel apparatus down the patient's arms and legs or other areas of the body. The points on the rotating pinwheel offer the risk of puncturing the skin and drawing blood. Therefore a risk factor is involved, not only to the patient but also to the examiner for the transference of any blood borne disease by this mechanism.

Up to the present time the pinwheel device available has been made of stainless steel. This device is generally used on a daily basis but it should require sterilization after each use to completely remove the possibility of transmitting a blood borne disease. The frequency of use and the problems of sterilization have discouraged the use of this instrument in favor of safety pins and toothpicks. These items are inappropriate substitutes, since they are largely inaccurate and time consuming.

The standard pinwheel apparatus consists of a stainless steel pinwheel rotatably attached by means of a screw to a stainless steel handle. This device has been used routinely by medical physicians, chiropractic physicians, osteopathic physicians, physicians' aides, nurse/practitioners, etc.

OBJECTIVES

It is an object of this invention to design a testing device of the rotatable pinwheel type in which the pinwheel is easily rotatably attached to the remainder of the device.

It is also an object of this invention that both the pinwheel and the remainder of the device may be made of a plastic.

It is also an object of this invention that the use of a plastic in this device facilitates the manner of assembly of the same.

It is also an object of this invention that the pinwheel device may be easily sterilized.

It is also an object of this invention that the sterilized device may be packaged and sealed in a sterile package.

It is also an object of this invention that the sterile device sealed in the sterile package may be stored until needed for its testing purpose.

Other objects will become apparent upon reading the description of this invention which follows.

SUMMARY

In accordance with the present invention a pinwheel, consisting of a disk with pointed projections extending outwardly from the circumference of the disk, is easily and rotatably mounted into the inside faces of the prongs of a two-pronged fork or yoke. By reference to the "inside faces of the prongs" is meant the faces of the prongs which face each other. This yoke or two-pronged fork is attached to and is an extension of a handle portion. Starting with the handle which may be any appropriate size and shape which will facilitate the examining physician's handling and use of the device, this handle has a first end and a second end. The first end is the portion held in the examiner's or operator's hand. The second end has a disk holding attachment with a two-prong shape or the shape of a U with the vertical portions of the U extended to form a two-prong shape as in a two-prong fork. The prongs are parallel to each other and the distance between the inside surfaces of the prongs, that is the surfaces facing each other, is only slightly more than the thickness of the disk, so that when the disk is positioned between the prongs, the disk may rotate freely. The bottom of the U shape attachment is positioned at and attached to the second end of the handle. On the inside surface of each prong, that is the surfaces facing each other, there i s a means adapted to receive and hold whatever means is used to rotatably hold the pinwheel or disk. Several of these holding means are described herein depending on the reciprocal means used at the center of each side of the disk. In each case the holding means is an appropriate distance from the bottom of the extended U shape so that the points extending from the disk will not touch the bottom of the extended U shape. The points or pins extending from the circumference of the disk extend in a direction in which the pins would be embraced by an extension of the disk if the disk were expanded to a larger circumference.

In one modification of this invention the disk has two short rods extending from and at the center of the disk, one on each side of the disk. The diameter of each rod is very slightly less than the width of a slot or groove cut into each of the two prongs. These slots are positioned so that each of the rods extending from the disk may be moved respectively into one of these slots. The mouth of each slot or groove is slightly narrower than the remainder of the slot so that pressure is required to push the rod past the mouth of the slot and further into the slot where the rod fits easily and permits rotation upon rotation of the disk. The narrowness of the mouth of the slot keeps the rod from sliding out of the slot without sideward pressure being exerted on the disk whereas the remainder of the slot is wide enough to permit free rotation of the rod. Generally there is no need to remove the disk from the holding arms. With both the disk and the holding arms and handle portion being made of a disposable plastic the assembled unit may be discarded. If the disk were to be removed and replaced by a new sterile disk, it would be advisable to sterilize the holder-handle portion of the device. However it is more advisable to sterilize the complete unit and package it in a sterile package for storage until needed. Preferably however the unit is prepackaged and then the unit and the package are sterilized together by gamma radiation. Other means of sterilization may be used if desired.

In other modifications it is possible to use two pivoting bosses and two recesses to receive the pivoting bosses so that the disk or pinwheel is freely rotatable. In one of these other modifications it is preferred to have the pivoting bosses on the inside surface of the two arms of the two-prong fork, that is on the arm surfaces facing each other in which case the recesses are individual recesses, one on one side and the other on the opposite side of the disk, both being at the center of the disk, or the recesses could be combined in an opening passing completely through at the center of the disk. With the arms being made of plastic the arms are resilient enough that pivot bosses on the inside of the arms could be pulled far enough apart to allow the disk to be slipped between the bosses until they reach the recesses in or the opening through the disk. Upon release of pressure on the arms, the pivot bosses will be positioned in the recesses or in the opening and the disk is freely rotatable on the pivot bosses.

In another modification using pivot bosses and recesses to receive the pivot bosses, the pivot bosses are positioned on the disk, one on each side of the disk and each positioned at the center of the disk. The recesses are positioned on the inside surfaces of the arms as previously described for the pivot bosses on the arms. The recesses are spaced from the bottom of the U shape a sufficient distance so that when the pivot bosses on the disk are positioned in the recesses on the arms, the points projecting from the disk will be spaced from and clear of the bottom of the U shape so that the disk may be rotated freely.

In addition to the advantage of disposability, the device of this invention when pivot bosses and accompanying recesses or openings are used to receive the pivot bosses, there is the advantage that the plastic is resilient enough to allow the arms to be pulled apart enough so that the pivot bosses and receiving recesses or openings can be pulled apart enough to put these into cooperating positions. This is not possible with the parts when they are made of stainless steel or other metal. While various plastics may be used in the manufacture of this device, such as polystyrene, polyethylene, etc., it is preferred to use polyurethane. Moreover parts for this device can advantageously be injection molded.

The description of the invention is facilitated by reference to the drawings.

BRIEF DESCRIPTION OF THE DRAWINGS

FIG. 5 is a side plan view of a preferred modification of the device of this invention in which two pivot bosses are used.

FIG. 6 is a front plan view of the modification of FIG. 5.

FIG. 7 is a side plan view of the pinwheel used in the devices of this invention.

FIG. 8 is a front plan view of the pinwheel of FIG. 7.

FIG. 9 is a partial cross-sectional view of the upper section of the modification shown in FIG. 6.

FIG. 10 is another partial cross-sectional view of FIG. 7 but showing a different arrangement of pivot bosses as shown in FIG. 8.

DETAILED DESCRIPTION

Figure 1:
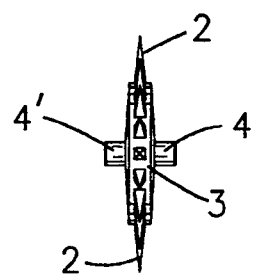
FIG. 1 is a front plan view of a pinwheel used in one modification of this invention.
Figure 2:
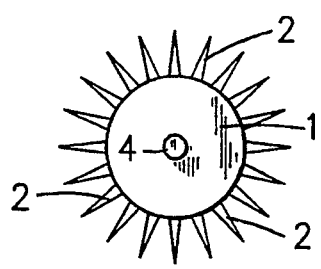
FIG. 2 is a side plan view of the pinwheel of FIG. 1.

In FIGS. 1 and 2, disk 1 has pointed projections or pins extending outwardly from the circumference 3. Generally there are between 20 and 50, preferably about 40 such pins. Rods 4 and 4' extend outwardly from the center on the sides of the disk 1, one on one side and the other on the other side. Preferably rods 4 and 4' each have length no greater than the thickness of each of arms 6 and 6'. Moreover the distance between arms 6 and 6' is only slightly greater than the thickness of disk 1.

Figures 3, 4:
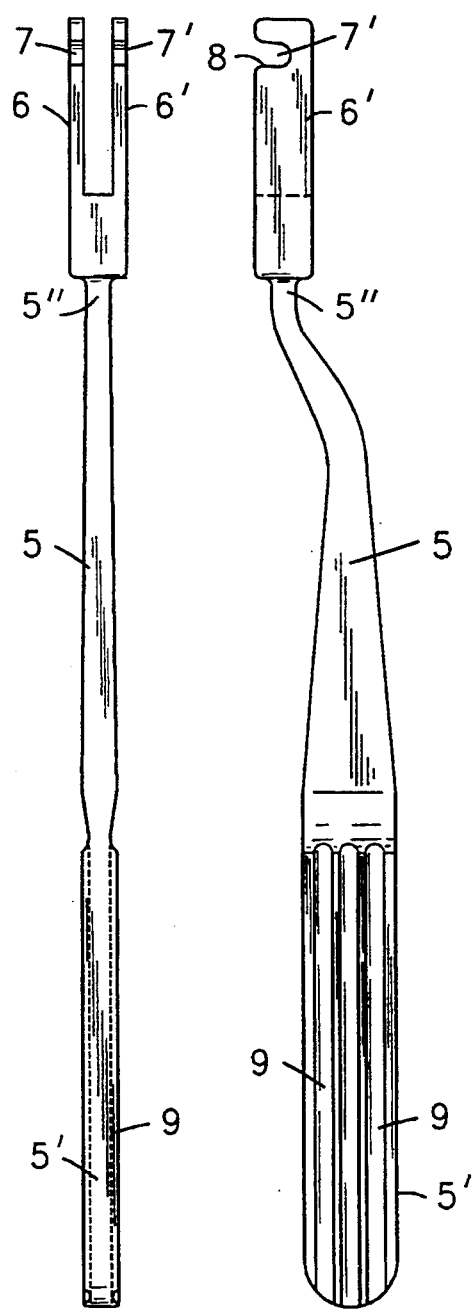
FIG. 3 is a front plan view of a handle and a two-prong fork used with the pinwheel of FIGS. 1 and 2.
FIG. 4 is a side plan view of the handle and two-prong fork of FIG. 3.

In FIG. 3 handle 5 has at its lower end the portion 5' which the operator holds in his hand. The opposite or upper end 5" has a U-shaped attachment with the sides or arms 6 and 6' of prolonged extension to give a shape also resembling a yoke. Arms 6 and 6' each have a slot 7 (and 7') cut completely through arms 6 and 6' and extending inwardly a sufficient distance that rod 4(or 4') can fit easily in the wider part of the slot and be free to permit rotation of the rod and with it rotation of the disk 3. The initial part 8 of slot 7' (and 7) is narrower than the remaining width of slot 7' (and 7). This narrowness at bulge 8 is such that rod 4 (and 4') can be pressed into the slot by exerting an inward pressure on the disk 1 to force it past bulge 8 or the narrower section of the slot 7 (and 7'). This restriction in the passageway prevents the rod 4(or 4') from slipping out from the slot when the disk is being freely rotated while rods 4 and 4' are rotating in the inner portion of slots 7 and 7 ' respectively. Here again in addition to disposability of the device when it is made of plastic, there is the added advantage of resiliency when rods 4 and 4' are being pressed into slots 7 and 7' past the restriction at the mouth of the slot. Ridges 9 are provided to facilitate gripping of handle 5'.

In FIGS. 5 and 6 pinwheel 10 is positioned between arms 16 and 16 '. Pinwheel 10 comprises disk 11 having pins or points 12 projecting outwardly from the circumference 13 of the disk. The center of disk 11 has a circle 14 which can represent an opening as shown in FIG. 9 or a pivot boss as shown in FIG. 10. The bottom of the elongated U-shaped yolk or two-pronged fork which embodies arms 16 and 16 ' is joined to the upper end 15' of handle 15. Preferably handle 15 is short and squat as compared to the longer handle of FIGS. 3 and 4 particularly in view of the use of plastic in making this disposable device.

FIG. 9 shows a preferred modification in which opening 14' extends through the center of disk 11 and cooperates with pivot bosses 17 and 17 ' which are positioned on the inside surfaces 20 and 20' respectively of arms 16 and 16'. The opening 14' conforms in size so that it fits onto pivot bosses 17 and 17' and the fit is such that the disk can freely rotate about the pivot bosses.

FIG. 10 shows another preferred modification in that the pivot bosses 17" and 17''' are positioned respectively on the disk and at the centers of the two sides thereof as shown in FIG. 10. These pivot bosses are positioned respectively in openings 18 and 18' which are positioned opposite each other on the inside faces 19 and 19' of arms 16" and 16'''.

Figure 11:
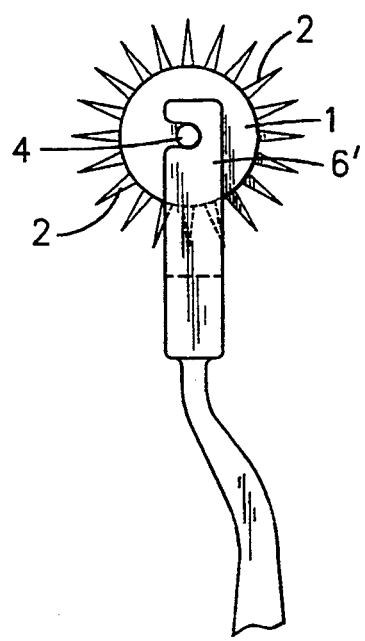
FIG. 11 is a plan view showing the assembly of the pin wheel of FIG. 2 on the upper portion of the holder of FIG. 4.

FIG. 11 shows the pinwheel of FIG. 2 assembled on the upper portion of the holder shown in FIG. 4.

In the plastics molding art the expression "pivot boss" is used to mean a round protuberance or knob which extends from the surface of one molded part which is positioned to cooperate with an opening or a recess in another part which is to be placed against the first part. The size and shape of the boss conforms to that required to fit the recess or opening and allow free rotation. The recess is positioned in the second molded part to be opposite and in a receiving position to have the "pivot boss" fit into the recess or opening. This positioning makes it possible to rotate the first part with respect to the second part and vice versa.

With respect to the "handle" this can be of various shapes, either long or narrow as in FIGS. 3 and 4 or relatively short and squat as in FIGS. 5 and 6. These and other shapes and sizes are suitable so long as they are easily "handable" and perform their functions as described herein.

When reference is made to the distance of the radius of the disk plus the pointed projection, this distance may also be described as the distance from the point of a pin to the center of the disk.

A disk is generally considered as having two flat sides and the "disk" expression is used herein since the sides are substantially flat with a slightly greater thickness in the center portion as shown more accurately in FIGS. 6 and 8.

While certain features of this invention have been described in detail with respect to various embodiments thereof, it will of course be apparent that other modifications can be made within the spirit and scope of this invention and it is not intended to limit the invention to the exact details shown above except insofar as they are defined in the following claims.

The invention claim is:

1. A device for testing a patient's sensation for pain comprising:
   (a) a handle having a first end and a second end, said first end being adapted to being held by an examiner testing a patient's reaction to pain and touch, and said second end having attached thereto two upwardly extending arms projecting in a U-shape with the two upwardly extending arms said U-shape being prolonged to resemble a two-pronged fork, said second end of said handle being attached to the bottom of said prolonged U-shape;
   (b) a disk having a circumference and two sides, said disk at each side thereof having a center and having at each said center a means by which said disk may be rotatably attached to said two upwardly extending arms, said disk having a plurality of points projecting outwardly from said circumference;
   said extending arms each having a receiving means to rotatably receive said disk at the center of said disk, said receiving means being positioned from the bottom of said U-shape a distance greater than the radius of said disk and the points projected therefrom whereby said disk may be rotated on its center without contact of the projected points on said disk with the bottom of said U-shape, whereby said examiner may freely rotate said disk with said projected points pressed into contact with a patient's test area; both said disk and said handle being made of a plastic.

2. A device for testing a patient's sensation for pain comprising:
   (a) a handle having a first end and a second end, said first end being adapted to being held by an examiner testing a patient's reaction to pain and touch, and said second end having attached thereto two upwardly extending arms projecting in a U-shape with the two upwardly extending arms of said U-shape being prolonged to resemble a two-pronged fork, said second end of said handle being attached to the bottom of said prolonged U-shape;
   (b) a disk having a circumference and two sides, said disk at each side thereof having a center and having at each said center a means by which said disk may be rotatably attached to said two upwardly extending arms, said disk having a plurality of points projecting outwardly from said circumference;
   said extending arms each having a receiving means to rotatably receive said disk at the center of said disk, said receiving means being positioned from the bottom of said U-shape a distance greater than the radius of said disk and the points projected therefrom whereby said disk may be rotated on its center without contact of the projected points on said disk with the bottom of said U-shape, whereby said examiner may freely rotate said disk with said projected points pressed into contact with a patient's test area both said disk and said handle being made of a plastic;
   in which said means by which said disk may be rotatably attached to said upwardly extending arms comprises said disk having a short rod protruding outward from each side of said disk and at the center of each side of said disk, and said two arms each having an opening positioned opposite to each other and extending inwardly from an outer edge of said arm to a point deep enough toward the opposite side of said arm whereby said opening is only large enough at its innermost region to receive one of said short rods and allow easy rotation of said disk on said rod, and said opening at said outer edge of said arm having a narrower dimension so that said rod may be permitted to enter said innermost portion of said opening only by applying pressure on said rod to force said rod into said innermost region of said opening in which said rod and said disk are easily rotatable, the position of each of said openings in said arms being spaced from the bottom of said U-shape a distance greater than the radius of said disk and the points projecting therefrom.

3. The device of claim 1 in which each said receiving means is a pivot boss facing inwardly toward the opposite arm; said disk has at each side thereof and at the center of each said side an opening extending at least partway into the interior of said disk and adapted to receive one of said pivot bosses, whereby said disk may be freely rotated on said pivot bosses.

4. The device of claim 3 in which said openings at the center of said disk comprise a single opening extending all the way through said disk.

5. The device of claim 1 in which each said arm has an opening positioned on that surface of said arm which faces the opposite arm, said disk has at each side thereof and at the center of said disk a pivot boss adapted to be received in one of said openings on said arms, the position of said openings being opposite to each other and adapted to receive one of said pivot bosses on said disk, the position of each said openings on said arms being spaced from the bottom of said U-shape a distance greater than the radius of said disk and the points projecting therefrom, whereby said disk may be rotated freely on its center without contact of said projected points with the bottom of said U-shape.

6. A device for testing a patient's sensation for pain comprising:
   (a) a handle having a first end and a second end, said first end being adapted to being held by an examiner testing a patient's reaction to pain and touch, and said second end having two arms projecting in a U-shape with the two upwardly extending arms of said U-shape being substantially prolonged to resemble a two-pronged fork, said second end of said handle and the bottom of said prolonged U-shape being positioned adjacent to and attached to said second end of said handle;

(b) a disk having a circumference and two sides, said disk at each side thereof having a center and having at each said center, an opening extending at least partially into the interior of said disk and said disk having a plurality of points projecting outwardly from said circumference;

(c) each said upwardly extending arm having an inside surface which faces toward the other said arm and an outside surface which faces away from the other said arm, each said inside surface having a pivot boss spaced from the bottom of said U-shape a distance greater than the radius of said disk and the points projecting therefrom, and said pivot bosses being positioned opposite to each other; whereby when said pivot bosses are individually introduced into said disk openings, said disk may be freely rotated without said projecting points coming into contact with the bottom of said U-shape; both said disk and said disk handle plus U-shaped extension being made of a plastic.

7. The device of claim 6 in which said handle is predominantly in a plane perpendicular to the plane of said points projecting from said disk.

8. The disk of claim 7 in which said handle has a width in the range of 0.5 to 1.5 inches and a length in the range of 1 inch to 3 inches.

9. A device for testing a patient's sensation for pain comprising:

(a) a handle having a first end and a second end, said first end being adapted to being held by an examiner testing a patient's reaction to pain and touch, and said second end having two arms projecting in a U-shape with the two upwardly extending arms of said U-shape being substantially prolonged to resemble a two-pronged fork, said second end of said handle and the bottom of said prolonged U-shape being positioned adjacent to and attached to said second end of said handle;

(b) a disk having a circumference and two sides, said disk at each side thereof having a center and having at each said center, a pivot boss extending outwardly a short distance and said disk having a plurality of points projecting outwardly from said circumference;

(c) each said upwardly extending arm having an inside surface which faces toward the other said arm and an outside surface which faces away from the other said arm, each said inside surface having an opening spaced from the bottom of said U-shape a distance greater than the radius of said disk and the points projecting therefrom, said openings being positioned opposite to each other, and when said disk is positioned between said two said arms and said pivot bosses are positioned in said disk openings, said disk may be freely rotated without said projecting points coming into contact with the bottom of said U-shape; both said disk and said handle plus U-shaped extension being made of a plastic.

10. The device of claim 1 in which said plastic is polyurethane.

11. The device of claim 5 in which said plastic is polyurethane.

12. The device of claim 6 in which said plastic is polyurethane.

13. The device of claim 9 in which said plastic is polyurethane.

* * * * *